United States Patent [19]

Cipullo

[11] Patent Number: 5,146,007
[45] Date of Patent: Sep. 8, 1992

[54] PROCESS FOR PREPARING BISPHENOL-A

[75] Inventor: Michael J. Cipullo, Mt. Vernon, Ind.

[73] Assignee: General Electric Company, Mt. Vernon, Ind.

[21] Appl. No.: 715,954

[22] Filed: Jun. 17, 1991

[51] Int. Cl.$^5$ .................. C07C 37/20; C07C 39/14
[52] U.S. Cl. ............................... 568/727; 568/722; 568/728
[58] Field of Search ................ 568/722, 727, 728

[56] References Cited

U.S. PATENT DOCUMENTS 4,191,843  3/1980  Kwantes et al. ............... 568/727

FOREIGN PATENT DOCUMENTS 0045959  2/1982  European Pat. Off. .......... 568/727
1078741  4/1986  Japan ........................... 568/727

*Primary Examiner*—Werren B. Lone
*Attorney, Agent, or Firm*—Joseph Eisele; Martin Barancik

[57] ABSTRACT

In the preparation of bisphenol-A by condensation of phenol with acetone in the presence of an acidic ion-exchange resin catalyst, pretreatment of the catalyst to render it anhydrous comprises two steps to minimize resin degradation. In the first step, from 25 to 90 percent by weight of the resin associated water is removed by vaporization, and in the second step dehydration is completed by saturating the partially dehydrated catalyst with phenol. The advantage of the improvement in the process resides in a more efficient drying, requiring less time and minimal degradation of the resin structure.

3 Claims, No Drawings

PROCESS FOR PREPARING BISPHENOL-A

FIELD OF THE INVENTION

1. Field of the Invention

The invention relates to processes for the synthesis of dihydric phenols and more particularly to a process for preparing bisphenol-A.

2. Brief Description of Related Art

The dihydric phenol 2,2 bis(4-hydroxyphenyl) propane (commonly referred to as "bisphenol-A") is commercially prepared by condensing 2 moles of phenol with a mole of acetone in the presence of an acid catalyst. A mole of water co-product is coproduced.

A catalyst utilized in the commercial processes is a macro-reticular or gellular, acidic ion-exchange resin; see for example the U.S. Pat. No. 4,191,843 (Kwantes et al). These catalysts are the product of monoethylenically unsaturated monomers copolymerized with polyvinylidene monomers, as described for example in the U.S. Pat. No. 3,037,052 (Bortnick). Preferred macroreticular resins are sulfonated to position sulfonic acid groups, pendant from the aromatic nucleus of the vinylidene moiety; see the U.S. Pat. No. 3,037,052.

The above-described acid catalyst (sulfocationites) contains up to 40 to 85 percent by weight of water and are generally made available by the manufacturer in this hydrated state. The presence of the water will inhibit the desired catalyst activity in condensing phenol with acetone, because the water will bind to the sulfonic acid groups in competition with reactant. For this reason, Bortnick (U.S. Pat. No. 3,037,052) teaches one to dehydrate the catalyst prior to use. As a method of dehydration, Bortnick suggests "drying at 105° C. to about 125° C. at a pressure of 5 to 10 mm" or by azeotropic distillation with an organic liquid (column 4, lines 54–64).

Kwantes et al., describing in particular the preparation of bisphenols, states that "the reactor may be filled with the acid ion exchanger by any known technique. Such techniques include adding the desired amount of dry ion exchanger, water wet ion exchanger or slurry of the ion exchanger in the reactor"; see column 2, lines 51–55. Details of the drying procedure are not elaborated upon beyond stating that the reactor charged resin is "drained"; see Example 1.

In the commercially practiced processes for preparing bisphenol-A, acid ion-exchange resins are dried in the plant reactor (usually a column reactor) prior to initiation of the reaction between phenol and acetone. Drying is effected by passing phenol over the catalyst in the absence of acetone, to absorb and/or displace the water associated with the acid ion-exchange resin. Water that is absorbed or displaced by the phenol is removed from the resin bed as an effluent stream. The water is ultimately removed from the phenol effluent by employing conventional separation techniques such as distillation and extraction. Water removal causes a reduction of volume of the resin bed so that more resin can be subsequently added to the bed. The alternating steps of dehydration and resin addition are continued until the reactor is completely charged with a dehydrated resin. Then the desired condensation reaction is initiated.

The aforementioned dehydration procedure is time consuming, often requiring several weeks and results in substantial reactor down time. Where a plant utilizes large amounts of catalyst resin, resin addition and drying can take several months. Furthermore, cycles of resin addition and dehydration are known to stress and damage macro-reticular or gellular resin beads. This deleteriously affects reaction mixture flow in the reactor and pressure drop across the bed.

One solution considered for the problems associated with the practiced procedure of drying the acidic ion-exchange resin it to follow the teachings of the aforementioned U.S. Pat. No. 3,037,052, and pre-dry the resin to an anhydrous state before it is charged to the column reactor. However, this procedure also has certain disadvantages. For example, if the resin is not rapidly dried under elevated temperature conditions (circa 150° C.), Zundel et al. has reported (Physik. Chem. (Frankfurt) 59, 225 [1968]) that the water is hydrogen bonded to three sulfonic acid groups and cannot be removed even under severe drying conditions. However, if drying is carried out at too rapid a rate, the resin beads may be subjected to abrasion and damage with a resultant loss of operating life. Clearly, the rate of drying is critical to an economic process.

According to the process of the invention, the hydrated catalyst is initially dried to remove a limited portion of the associated water content. This is carried out in a manner designed to minimize changes in the resin bed volume. Then, dehydration is completed with the known and practiced procedure of water absorbtion/displacement from the resin with phenol. Resin volume changes are held to a minimum, thereby avoiding resin degradation. Advantageously, the total time required in a commercial plant for charging and drying the resin is substantially reduced.

SUMMARY OF THE INVENTION

The invention comprises a process for the preparation of bisphenol-A, which comprises;

providing a hydrated acidic ion-exchange resin catalyst for catalyzing the condensation of phenol with acetone;

vaporizing a portion of the water associated with the hydrated catalyst;

separating sufficient of the water vapor from the catalyst to remove from about 25 to about 80 percent by weight of said water, whereby a partially dehydrated catalyst is obtained;

contracting the partially dehydrated catalyst with phenol so as to remove additional water from the catalyst until the water content of the effluent phenol contains less than about 4 weight percent water; and condensing phenol and acetone in the presence of the dehydrated catalyst.

DETAILED DESCRIPTION OF THE PREFERRED EMBODIMENTS OF THE INVENTION

Acidic ion-exchange resins useful to catalyze the condensation of phenol with acetone are generally well known compositions as are methods of their preparation; see for example the preparative procedures described in U.S. Pat. No. 3,037,052 which is hereby incorporated by reference thereto. Representative of acid ion-exchange resins are strong-acid ion exchangers, such as those resins or polymers having a plurality of pendant sulfonic acid groups. Examples include sulphonated polystyrene or poly(styrene-divinylbenzene) copolymer and sulphonated phenol-formaldehyde resins. The sulphonated resins are commercially available in water swollen form as gellular, micro-reticular and macro-reticular types. Specific examples of suitable resins are Amberlite IR-120H, Amberlyst 15H, Amberlyst 31, Dowex 50-X-4. Dowex MSC-1H, Duolite c-26, Permutit QH, Chempro C-2 and Imac C8P/H (Amberlite, Amberlyst, Dowex, Duolite, Permutit, Chempro and Imac are registered U.S. Trademarks). Further examples of such ion exchangers as well as methods for preparing such ion exchangers are described in the Encyclopedia of Polymer Science and Technology, 1967, vol. 7, pages 695 to 708. The exchange capacity of the acidic resin is preferably at least 2.0 meq. $H^+/g$ of dry resin, with exchange capacities in the range of from 3.0 to 5.5 meq. $H^+/g$ (dry resin) particularly preferred. One preferred catalyst used in the process of the present invention is the Amberlyst ® gellular types, which are styrene cross-linked with divinylbenzene or like crosslinking monomer and having pendant sulfonic sulfonic acid groups attached to the aromatic nucleus of the styrene moiety. Sulfonation may be by the process described in U.S. Pat. No. 2,366,007 which is incorporated herein by reference thereto.

Advantageously, catalyst drying is carried out by first heating the water saturated catalyst to vaporize the water, entrain the vapors in a moving gas (air, inert gas such as nitrogen) and separate a portion of the vapors from the catalyst. The weight proportion of water vaporized and removed from the catalyst can vary, but the preferred amount of water remaining in the catalyst is generally within the range of from 2 to 50 percent.

In the process of the invention, the resin catalyst is not rendered anhydrous by the initial drying through vaporization of the water content. Removal of the water content shrinks the resin volume and potentially degrades resin structure. Reducing the water content partially, preferably to the point where the catalyst resin volume is near (plus or minus about 25 percent by volume) that of the phenol saturated resin volume, is advantageous. For example, reducing the water content of a given 60 percent (by weight) water resin to a level of from 20 to 40 percent provides a resin occupying a volume approximately equal to the same resin saturated with phenol (appreciate that the solvent-retention capacity of an acidic ion-exchanger is a reproducible equilibrium quantity dependant upon ion-exchange capacity, ionic form, the solvent, the degree of cross-linking, temperature, humidity and other variable; see for example Helfferich, Ion Exchange, McGraw-Hill Book Co., Inc., New York, N.Y. [1962], Chapter 5). Thus, passing phenol through a reactor containing this particular resin (initially with 20 to 40 weight percent of water will not significantly affect the resin volume, thereby minimizing degradation resulting from stresses during the drying and swelling procedures.

The partially dehydrated catalyst may be charged to an appropriate reactor, for example a fixed bed column reactor and saturated with phenol to complete dehydration. Alternatively, the wet ion exchange resin may be charged to the reaction zone and subjected to partial drying as described above in-situ, before saturation with phenol. The phenol addition may be carried out in the reactor or in a different vessel and then transferred to the reactor or reaction zone. The catalyst is further dried by the addition of phenol to the desired level of water content in the catalyst. This level of water will affect the rate of reaction between the phenol and acetone. Essentially about 4 weight percent water in the phenol effluent would bring about a marginally acceptable reaction rate while a level of about 2 weight percent in the effluent or less is preferred. A level of less than about 1 weight percent is most preferred. The reaction zone is then ready to receive acetone and a molar excess of phenol for condensation following known procedures.

The reaction zone may comprise a single reactor or two or more reactors in series or in parallel. In the case of a multi-reactor reaction zone, suitably all of the phenol is fed to the first reactor and the acetone compound is either fed all to the first reactor or divided between the first and second and possibly further reactors.

The molar ratio of phenol to acetone is at least 2 to 1 with a stoichiometric excess of phenol being preferred. Molar ratios are preferably from 3:1 to 40:1, with molar ratios of from 10:1 to 30:1 being most preferred. The optimum ratio depends on reaction conditions, e.g., temperature of reaction and desired conversion.

The reaction temperature in the reactor zone may vary from 40° C. to 95° C. with reaction temperatures in the range of from 55° C. to 90° C. being preferred.

The reaction time in the reactor zone may also vary and depend on reaction temperature. For example, the liquid hour space velocity (LHSV) of the feed may vary between wide limits with velocities in the range of from 0.2 to 40 liters feedstream/liter catalyst$^{-1}$/hour$^{-1}$.

The following example describes the manner and process of making and using the invention and sets forth the best mode contemplated by the inventors for carrying out the invention.

PREPARATION

A quantity of a gellular acidic ion exchange resin of the sulfonated type (Amberlyst 31, Rohm and Haas Company) having a water content of 60 percent by weight is partially dehydrated in a drying oven to a water content of about 30 percent.

For testing purposes, a sample of this partially dried resin was immersed in phenol and observed to swell approximately 10%. Samples of this swelled resin were observed under a microscope both before and after this phenol contact to determine if the resin structure had been affected. The resin beads were found to have retained their structural integrity in a sense that they were of uniform size, with no cracks. Similar samples of resin which was previously completely dried (<1% water) were found to contain many cracked beads and bead fragments due to much larger swell (>40%) when contacted with phenol in a similar manner.

EXAMPLE

A tubular reactor is charged with a quantity of 30 weight percent water content resin as prepared in the first paragraph of Preparation 1 and dried further by passing phenol over the resin bed. When test samples show the phenol effluent has less than 1% water, a feedstream comprising phenol and acetone (mole ratio 15:1) is continuously passed through the reactor at a liquid hour space velocity of 5 liters/liter catalyst$^{-1}$/hour$^{-2}$ and the reaction zone effluent continuously withdrawn and fed to a purification system for separation of the product bisphenol-A.

In the claims:

1. A process for the preparation of bisphenol-A, which comprises;
    providing a hydrated acidic ion-exchange resin catalyst for catalyzing the condensation of phenol with acetone;

vaporizing a portion of the water associated with the hydrated catalyst;

separating sufficient of the water vapor from the catalyst to remove from 25 to 90 percent by weight of said water, whereby a partially dehydrated catalyst is obtained; and contacting the partially dehydrated catalyst with phenol so as to remove additional water from the catalyst until the water content of the effluent phenol contains less than about 4 weight percent water; and condensing phenol and acetone in a reaction zone at a temperature within the range of from 40° to 95° C., in the presence of the dehydrated catalyst.

2. A process of claim 1 wherein the resin catalyst is gellular.

3. A process of claim 1 wherein the level of dehydration is brought to less than about 1 weight percent water.

* * * * *